(12) United States Patent
Cortellessa et al.

(10) Patent No.: US 7,101,377 B2
(45) Date of Patent: Sep. 5, 2006

(54) DEVICE FOR OPTIMIZING A KNEE ENDOPROSTHESIS

(75) Inventors: Maurizio Cortellessa, Burgdorf (CH); Roland Herzog, Waldenburg (CH); Ate B. Wymenga, Sintmaartenskliniek, Hegstdal 3, Nijmegen (NL) NL-6522 Jv

(73) Assignee: Ate B. Wymenga, Arnhem (NL)

( * ) Notice: Subject to any disclaimer, the term of this patent is extended or adjusted under 35 U.S.C. 154(b) by 574 days.

(21) Appl. No.: 10/362,147

(22) PCT Filed: Jul. 9, 2001

(86) PCT No.: PCT/CH01/00426

§ 371 (c)(1),
(2), (4) Date: Aug. 11, 2003

(87) PCT Pub. No.: WO02/17826

PCT Pub. Date: Mar. 7, 2002

(65) Prior Publication Data
US 2004/0039398 A1    Feb. 26, 2004

(30) Foreign Application Priority Data
Aug. 19, 2000 (DE) ............................. 200 14 377

(51) Int. Cl.
A61B 17/56 (2006.01)
(52) U.S. Cl. .................................................. 606/102
(58) Field of Classification Search ............ 606/102, 606/87, 88, 89
See application file for complete search history.

(56) References Cited

U.S. PATENT DOCUMENTS

| | | | |
|---|---|---|---|
| 4,524,766 A | 6/1985 | Petersen |
| 5,540,696 A | 7/1996 | Booth, Jr. et al. |
| 5,720,752 A | 2/1998 | Elliot et al. |
| 5,810,831 A | 9/1998 | D'Antonio |
| 5,925,049 A | 7/1999 | Gustilo et al. |
| 6,056,756 A | 5/2000 | Eng et al. |
| 6,173,200 B1 | 1/2001 | Cooke et al. |

FOREIGN PATENT DOCUMENTS

EP    1 033 117 A2    9/2000

*Primary Examiner*—Eduardo C. Robert
*Assistant Examiner*—David Comstock
(74) *Attorney, Agent, or Firm*—Rankin, Hill, Porter & Clark LLP

(57) ABSTRACT

A device for determining the optimal dimensions of the components of a knee endoprosthesis, including A) an angular element (7) having a first anterior plate (9) and a second distal plate (10) that is arranged at right-angle thereto; B) a first caliper (16) that is arranged on the second plate (10) in a manner that permits it to be displaced parallel to the central axis (19) and to be arrested, and which has a bearing surface (25), the bearing surface being essentially parallel to the first plate (9) and provided for resting against a tibial plateau (29) when a knee joint is bent; and, C) a second caliper (11) that is arranged in a manner that permits the second caliper to be displaced parallel to the longitudinal axis (8) of the first plate (9) and to be arrested, and which has a bearing surface (24), the bearing surface being essentially parallel to the inner side (23) of the second plate (10) and provided for resting against the tibial plateau (29) when the knee joint is straightened.

10 Claims, 4 Drawing Sheets

DEVICE FOR OPTIMIZING A KNEE ENDOPROSTHESIS

The invention relates to a device permitting to determine the optimal dimensions of individual components of a knee endoprosthesis as claimed in the precharacterising part of claim 1.

A device comprising a plurality of alignment and guide appliances is known from U.S. Pat. No. 4,524,766 PETERSEN. One of these guides comprises an L-shaped plate having a spacer and a foot which is aligned and fixed on the femur. This guide serves on the one hand for guiding the cutting tool during the anterior femoral resection and, on the other hand, for planning the height of the posterior femoral resection, the spacer serving for adjusting the distance to be observed between the femur and the tibia while the knee joint is bent. Said distance, which is to be adjusted in accordance with the thickness of the tibial component to be implanted, may be read form a scale present on the plate. After that, another guide serving for the distal resection of the femoral condyles is affixed to the tibia. Said second guide includes a guide element which is adjustable with respect to the height of the tibial component to be implanted.

In this known device, the tension of the ligaments is considered only in a bent condition of the knee joint, during the application of the first guide. The guide for the distal resection of the femoral condyles while the knee is straightened is only adjustable with respect to the tibial component, without consideration of the tension of the ligaments.

In view of this shortcoming, it is an object of the invention to provide a device permitting to determine, for the entire ROM (range of motion), the optimum dimensions of the components of a knee endoprosthesis, said device being applicable in particular for revision purposes in knee alloarthroplasty.

The selectable dimensions essential for coordinated movement include the A/P size (anterior/posterior dimension) of the femoral component, the thickness of the polyethylene inlay (PE inlay) of the tibial component, and the thickness of the spacer located between the resected femoral surface and the femoral component. In addition, it is possible to determine the height of the resulting joint line as well as the external rotation of the femoral implant.

According to the invention, this object is achieved by means of a device which shows the features of claim 1.

The device is fixed on the distal, resected surface of the femur which serves as a surface of reference for the device. The proximal surface of the tibia is also resected, so as to form a further reference surface.

The device according to the invention for determining the optimal dimensions of the components of a knee endoprosthesis comprises an angular element affixable distally on the femur, a first calliper located on the posterior side (in flexion) and displaceable relative to said angular element, and a second calliper situated on the distal side (in extension) that is equally displaceable relative to the angular element. The angular element comprises a first plate having a bottom surface facing anteriorly towards the femur, a plate longitudinal axis extending parallel to said bottom surface and to the longitudinal axis of the femur, a proximal, first end portion and a second end portion intersecting the plate longitudinal axis and arranged distally to the femur, and a second plate extending perpendicularly to said bottom surface having a central axis extending perpendicularly to the plate longitudinal axis, an inner side capable of being brought to rest against the resected end face of the femur, and a bottom end portion arranged posteriorly to the femur.

The first calliper has a first bearing surface extending substantially parallel to the bottom surface and designed to rest against the proximal, resected tibial plateau when the knee joint is bent, it is displaceable parallel to the central axis and is releasably fastenable on the second plate. The second calliper has a second bearing surface extending substantially parallel to the inner surface and designed to rest against the proximal, resected tibial plateau when the knee joint is straightened, it is displaceable parallel to the plate longitudinal axis and is releasably fastenable on the first plate.

In the preferred embodiment of the device according to the invention, said device comprises a first inlay which is arranged between the posterior, bottom end portion of the second plate and the first calliper in such a way as to be displaceable coaxially to the central axis and is releasably fastenable on the second plate. A second inlay is arranged between the distal, second end portion of the first plate and the second calliper in such a way as to be displaceable coaxially to the plate longitudinal axis and is releasably fastenable on the first plate. The inlays are embodied in such a way that the callipers are displaceable relative to the inlays in a direction parallel to the central axis and to the plate longitudinal axis, respectively.

In a further embodiment of the device according to the invention, the two callipers comprise positioning means which are arranged on a straight line extending parallel to the central axis and the plate longitudinal axis, respectively, and are spaced apart from one another in axial succession by the distances $a_j$, whereby the bearing surfaces of the callipers are fastenable at defined distances ($A_i = \Sigma a_j$; j=1 to N) relative to the inlays.

Furthermore, both inlays may be provided with positioning means which are equally arranged on a straight line extending parallel to the plate longitudinal axis and to the central axis, respectively, and are spaced apart from one another in axial succession by the distances $b_j$ for the second inlay and by the distances q for the first inlay, whereby the inlays are fastenable at the defined distances ($B_i = \Sigma b_j$; j=1 to M) and ($C_i = \Sigma c_j$; j=1 to Q), respectively, relative to the plates.

The desired amounts for the relevant values ($A_i$, $B_i$ or $C_i$) can easily be read on the device by the surgeon. For this purpose, marks indicating the different distances may be made on the device. The crucial ligaments are not taken into consideration by the device as the latter is primarily intended to be usable for revision purposes.

Preferably, the positioning means are grooves which are formed in the callipers and in the inlays in such a way that screws insertable into the plates may be made to releasably engage with the grooves.

The adjustment of the distances $A_i$, $B_i$, and $C_i$ on the device permits to simultaneously determine the A/P size of the femoral component by adjusting the distance $C_i$, the thickness of the polyethylene (PE) inlay of the tibial component by adjusting the distances $A_i$, the thickness of the spacer for the femoral component by adjusting the distance $B_i$ as well as the height of the resulting joint line and the external rotation of the femoral implant by checking the tension of the ligaments of the knee when the knee is bent (with the femur and the tibia forming an angle of 90 degrees between each other) and when the knee is straightened (with the femur and the tibia forming an angle of 0 degrees between each other).

These values are established before the A/P cuts and the oblique cuts are realised on the femur.

In a preferred improvement of the invention, the distances $A_i$ correspond to the different, standardised thicknesses of the inlay (PE-inlay) of the tibial component, the distances $B_i$ correspond to the different, standardized thicknesses of the spacer, and the distances $C_i$ permit to adjust the different, standardised A/P sizes of a femoral component of the knee endoprosthesis.

The advantages of the device according to the invention consist in the possibility to optimise the thickness of the inlay, the thickness of the spacer and the A/P size of the femoral component by an adequate adjustment of the movable parts of the device in such a way that the tension of the ligaments corresponds to that of a natural knee joint.

In the following, the invention and improvements of the invention will be illustrated in greater detail with reference to the partially diagrammatic representations of several embodiments.

Figure 1:
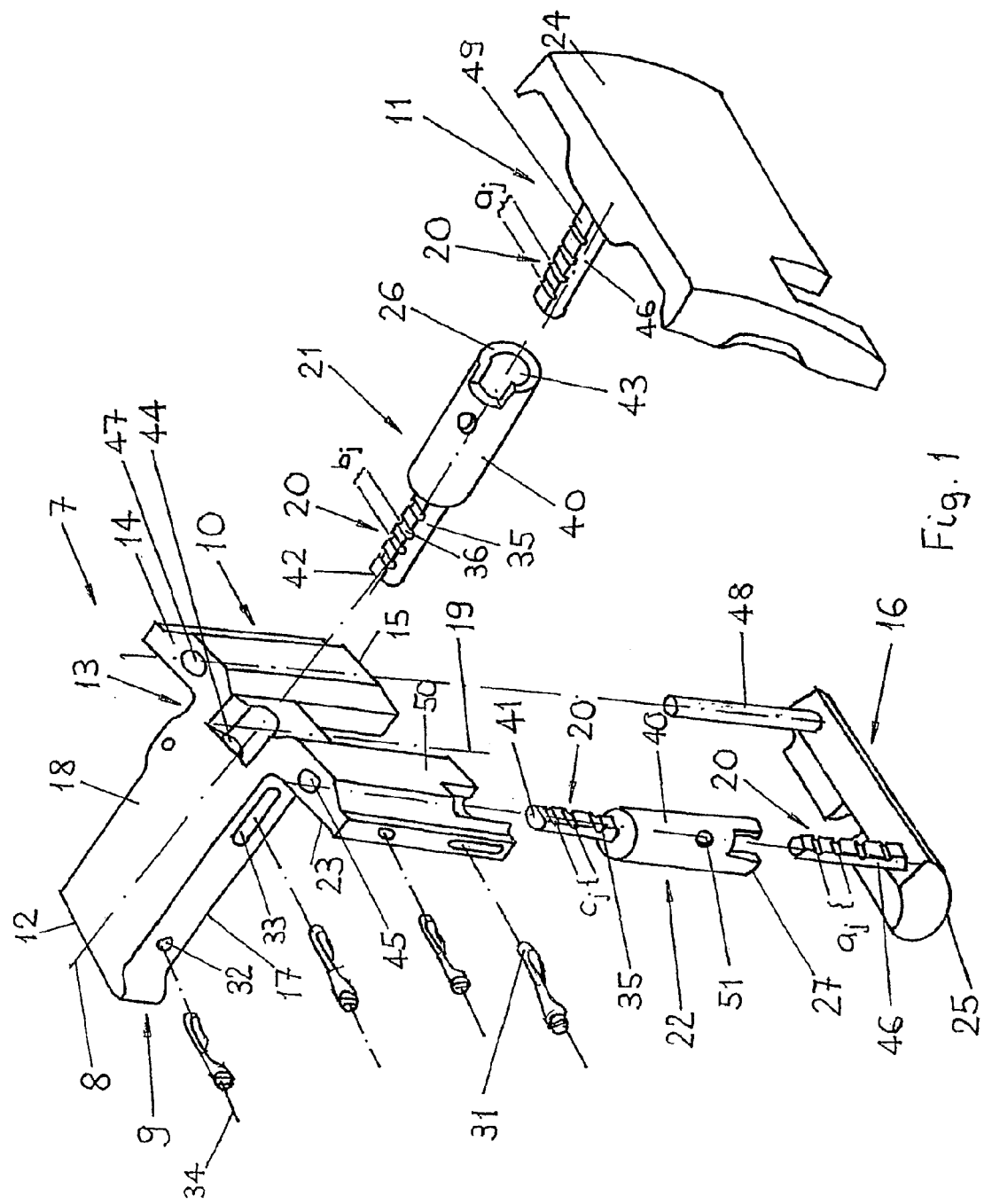
FIG. 1 is a perspective, exploded view of one embodiment of the device according to the invention.

FIG. 1 shows a preferred embodiment of the device according to the invention. This device comprises essentially an angular element 7 which consists of a first plate 9 arranged anteriorly on the femur 5 (FIG. 2) and having a longitudinal axis 8, and, arranged at a right angle thereto, of a second plate 10 arranged distally on the femur 5 (FIG. 2) and having a central axis 19 extending perpendicularly to the first plate 9, a first calliper 16 arranged posteriorly on the second plate 10 in such a way as to be displaceable, and releasably fastenable, parallel to the central axis 19, and a second calliper 11 arranged distally on the angular element 7. The first plate 9 comprises, posteriorly, a bottom surface 17 and, anteriorly, a top surface 18, a first end portion 12 proximally intersecting the plate longitudinal axis 8, and a second end portion 13 distally intersecting the plate longitudinal axis 8. The second plate 10 comprises anteriorly a top end portion 14, posteriorly a bottom end portion 15, and a substantially planar, inner side 23 adjoining the second end portion 13 so that the angular element 7 may be connected to the femur 5 in such a way that the inner side 23 may be brought to rest against the distal end face 28 of the femur and the first plate 9 is arranged anteriorly to the femur 5 with its longitudinal axis 8 extending parallel to the longitudinal axis of the femur 5. The angular element 7 is affixed to the femur 5 using an intramedullary rod 30 (FIG. 2) which is insertable into the intramedullary canal of the femur 5 in such a way as to be freely turnable therein. The first calliper 16 includes a first bearing surface 25 which extends substantially parallel to the bottom surface 17 of the first plate 9 and which may be brought to bear against the tibial plateau 29 when the knee joint is bent. The second calliper 11 is arranged on the second end portion 13 of the first plate 9 in such a way as to be displaceable, and releasably fastenable, parallel to the plate longitudinal axis 8, and includes a second bearing surface 24 which extends substantially parallel to the inner side 23 of the second plate 10 and may be brought to rest against the tibial plateau 29 when the knee joint is straightened.

Furthermore, the device comprises an inlay 22 which has a bottom end face 27 facing the first calliper 16, which is arranged coaxially to the central axis 19 so as to be displaceable between the bottom end portion 15 of the second plate 10 and the first calliper 16, and which is releasably fastened to the second plate 10, so that the inlay 22 is displaceable posteriorly relative to the second plate 10 while the first calliper 16 is displaceable relative to the first inlay 22 and, consequently, to the second plate 10.

By analogy, between the second end portion 13 of the first plate 9 and the second calliper 11, a second inlay 21 is inserted, which is provided with an anterior end face 26 facing the second calliper 11, and is arranged in such a way as to be displaceable coaxially to the plate longitudinal axis 8 and releasably fastenable to the first plate 9, so that the second inlay 21 is distally displaceable relative to the first plate 9 and the second calliper 11 is displaceable relative to the first inlay 22.

On the side opposite to the end face 27, the first inlay 22 is provided with a top end portion 41 and comprises, extending between the bottom end face 27 and the top end portion 41 and arranged axially adjacent to one another, a sleeve 40 and a pin 35. The sleeve 40 adjoins the bottom end face 27 and is provided with a sleeve bore 43 which is open towards the bottom end face 27. By analogy, the second inlay 21 has a posterior end portion 42 arranged on the side opposite to the anterior end face 26 and comprises, extending between the anterior end face 26 and the posterior end portion 42 and arranged axially adjacent to one another, a sleeve 40 and a pin 35, the sleeve 40 adjoining the anterior end face 26 and the sleeve bore 43 being open towards the anterior end face 26. For receiving, by way of axial displacement, the second inlay 21, the first plate 9 includes a first guide bore 44 extending coaxially to the plate longitudinal axis 8, whereas the second plate 10 comprises a second guide bore 45 extending parallel to the central axis 19 for receiving, by way of axial displacement, the first inlay 22, and comprises, in addition, a further bore 47, equally extending parallel to the central axis 19, for receiving, by way of axial displacement, a peg 48 connected to the first calliper 11. On their sides facing the first and the second bearing surfaces 25;24, respectively, the first and second callipers 16;11 are each provided with a guide bolt 46 which may be received, by way of axial displacement, in the sleeve bores 43, so that the first plate 9, the second inlay 21, and the second calliper 11 are axially telescopable relative to the plate longitudinal axis 8. On the other hand, the first inlay 22 and the first calliper 16 are axially telescopable relative to the central axis 19.

The second calliper 11 further comprises positioning means 20 which are arranged on a straight line extending parallel to the plate longitudinal axis 8 and are spaced apart from each other in axial succession by the distances $a_j$. By means of these positioning means 20, the second bearing surface 24 of the second calliper 11 may be fixed at the defined distances $(A_i = \Sigma a_j; j=1$ to $N)$ relative to the anterior end face 26 of the second inlay (FIG. 2).

Figure 2:
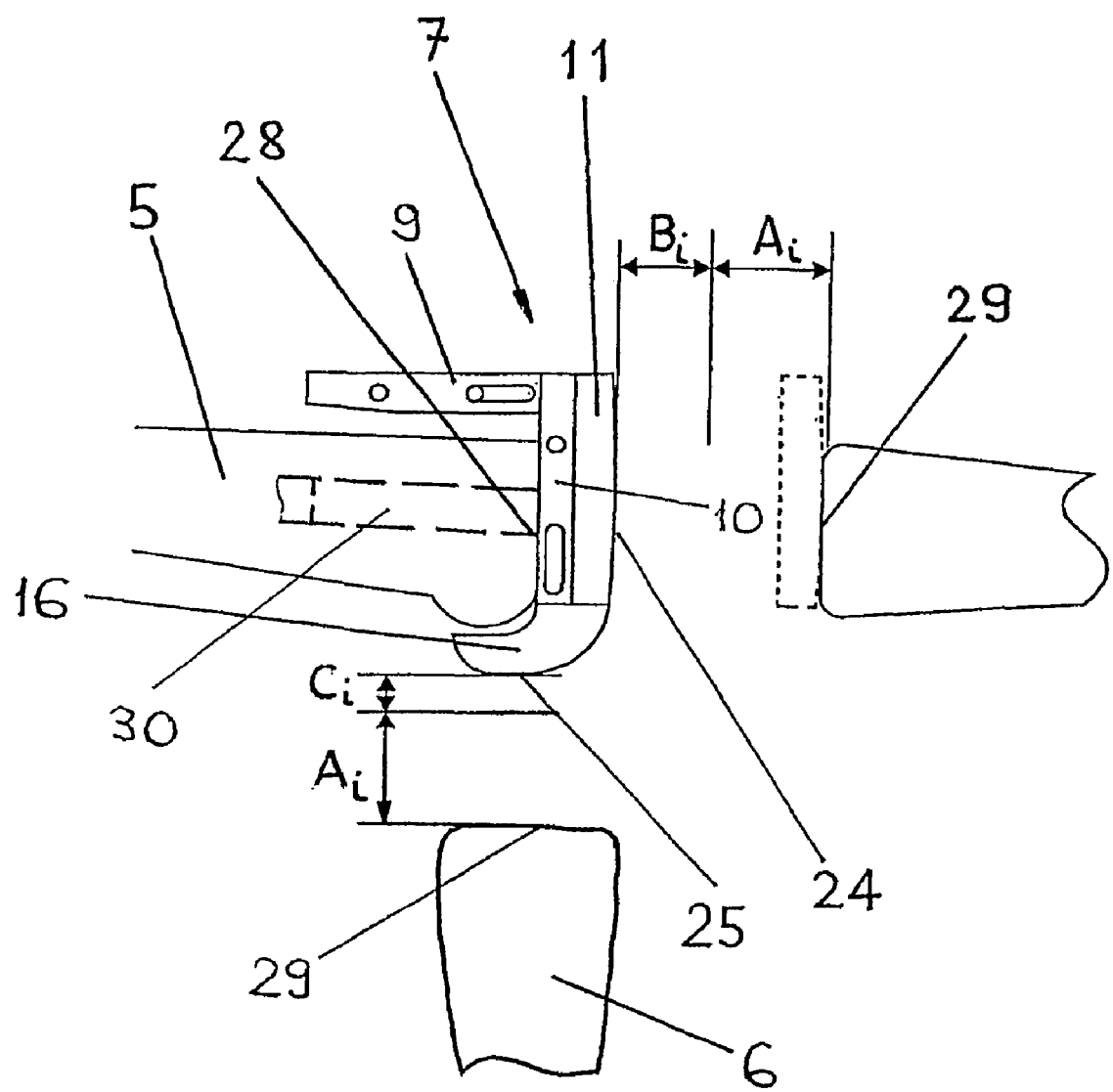
FIG. 2 shows a view of the device according to the invention represented in FIG. 1.

By analogy, the first calliper 16 comprises positioning means 20 which are arranged on a straight line extending parallel to the central axis 19 and are axially spaced apart from each other by the distances $a_j$, whereby the first bearing surface 25 of the first calliper 16 may be fixed at the defined distances $(a_i = \Sigma a_j; j=1$ to $N)$ relative to the bottom end face 27 of the first inlay 22 (FIG. 2).

The pins 35 provided on the first and second inlays 22;21, as well as the guide bolts 46 provided on the first and second callipers 16;11 have a cross section shaped in the form of a segment of a circle, the flats 49 facing towards the top surface 18 of the first plate 9 and towards the outer side 50 of the second plate 10, respectively. Grooves 36 which are sunk into these flats 49 form the positioning means 20 and extend crosswise relative to the plate longitudinal axis 8 and to the central axis 19, respectively. The axial arresting of the first and second inlays 22;21 relative to the first and second plates 9;10, respectively, is realised by means of location pins 31 which are lodged in an axially displaceable manner within the first and second plates 9;10 by means of first transverse bores 32 having bore axes 34 extending crosswise to the plate longitudinal axis 8 and to the central axis 19, respectively, said location pins being capable of engaging with the grooves 36 formed in the pins 35. The axial arresting of the first and second callipers 16;11 relative to the first and second inlays 22;21 is equally realised by means of such location pins 31 which are lodged in an axially displaceable manner within second transverse bores 51 formed in the first and second inlays 22;21 and may be brought to engage with the grooves 36 formed in the guide bolts 46. In order to assure that the first and second inlays 22;21 with arrested first and second callipers 6;11 remain nonetheless displaceable relative to the first and second plates 9;10, the first and second plates 9;10 are provided with elongate holes 33 having their longitudinal dimensions parallel to the plate longitudinal axis 8 and to the central axis 19, respectively, and which serve for receiving the location pins 31.

Figure 3:
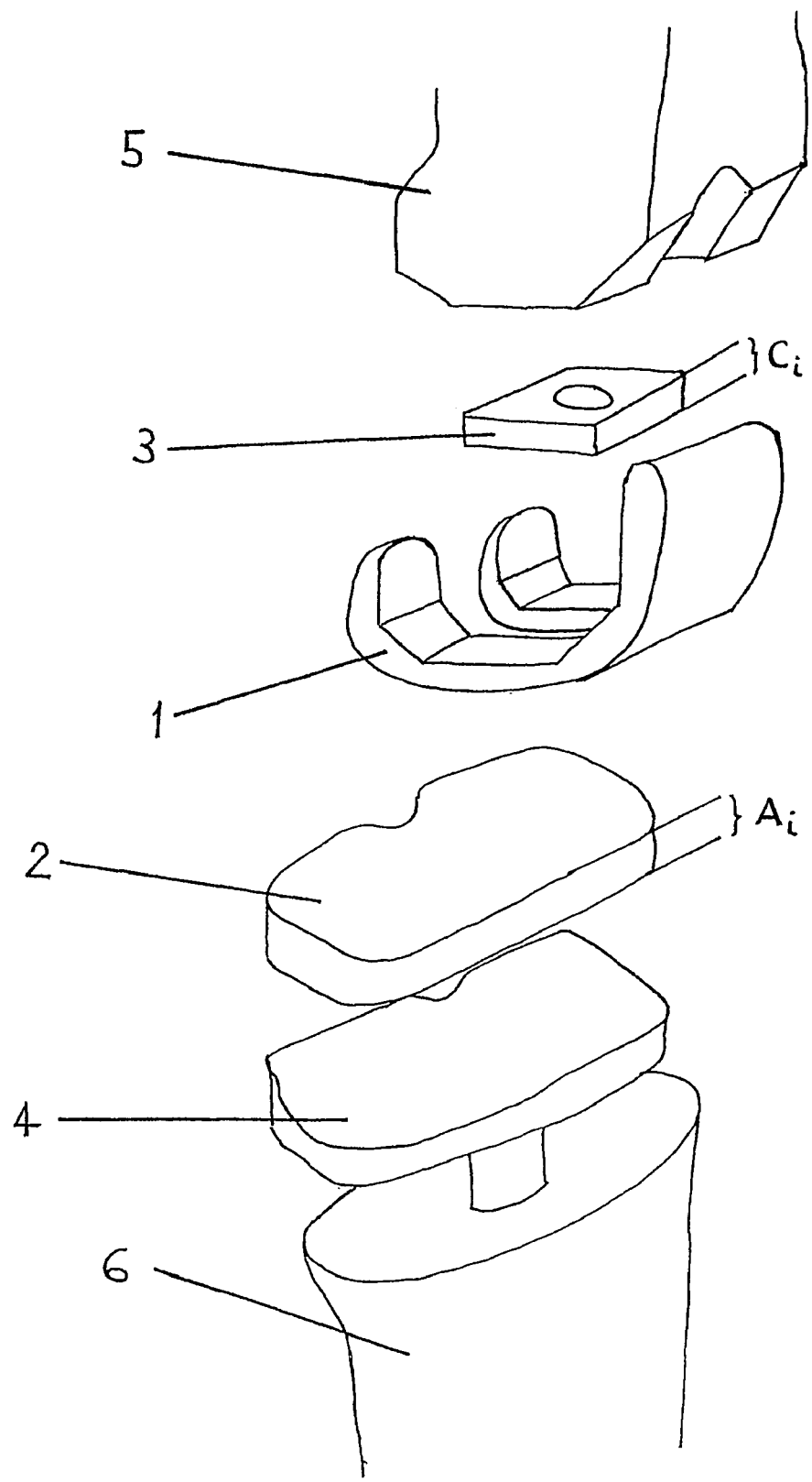
FIG. 3 shows a perspective view of a knee endoprosthesis.

The distances A correspond to the different, standardised thicknesses of an inlay 2 of the tibial component of a knee endoprosthesis (FIG. 3).

The second inlay 21 equally comprises positioning means 20 which are arranged on a straight line extending parallel to the plate longitudinal axis 8 and are spaced apart from one another in axial succession by the distances b. Thus, the anterior end face 26 of the second inlay 21 is adjustable at the defined distances ($B=\Sigma b$; $j=1$ to M) relative to the second end portion 13 of the first plate 9. These distances B correspond to the different, standardised thicknesses of a spacer 3 for the femoral component 1 of a knee endoprosthesis.

By analogy, the first inlay 22 comprises positioning means 20 which are arranged on a straight line extending parallel to the central axis 19 and are spaced apart from one another in axial succession by the distances $c_j$. Thus, the bottom end face 27 of the first inlay 22 may be fixed at the defined distances ($C_i=\Sigma c_j$; $j=1$ to Q) relative to the bottom end portion 15 of the second plate 10, the distances $C_i$ corresponding to the different, standardised A/P sizes 30 of a femoral component 1 of a knee endoprosthesis.

FIG. 3 shows an embodiment of a knee endoprosthesis represented together with a femur 5 and a tibia 6. The knee endoprosthesis is composed of a femoral component 1 with a selectable A/P size 30 (anterior/posterior size), a spacer 3 capable of being mounted between the femur 5 and the femoral component 1, a tibial component 4 and an inlay 2 located between the tibial component 4 and the femoral component 1. The thickness $a_i$ of the inlay 2, measured in an axial direction with respect to the longitudinal axis of the bone, the distance $C_i$ of the spacer 3, equally measured in an axial direction with respect to the longitudinal axis of the bone, and the anterior/posterior size 30 of the femoral component 1, measured in an anterior/posterior direction perpendicularly to the longitudinal axis of the bone, represent the dimensions of the knee endoprosthesis which may be determined with the aid of the device according to the invention.

Figure 4:
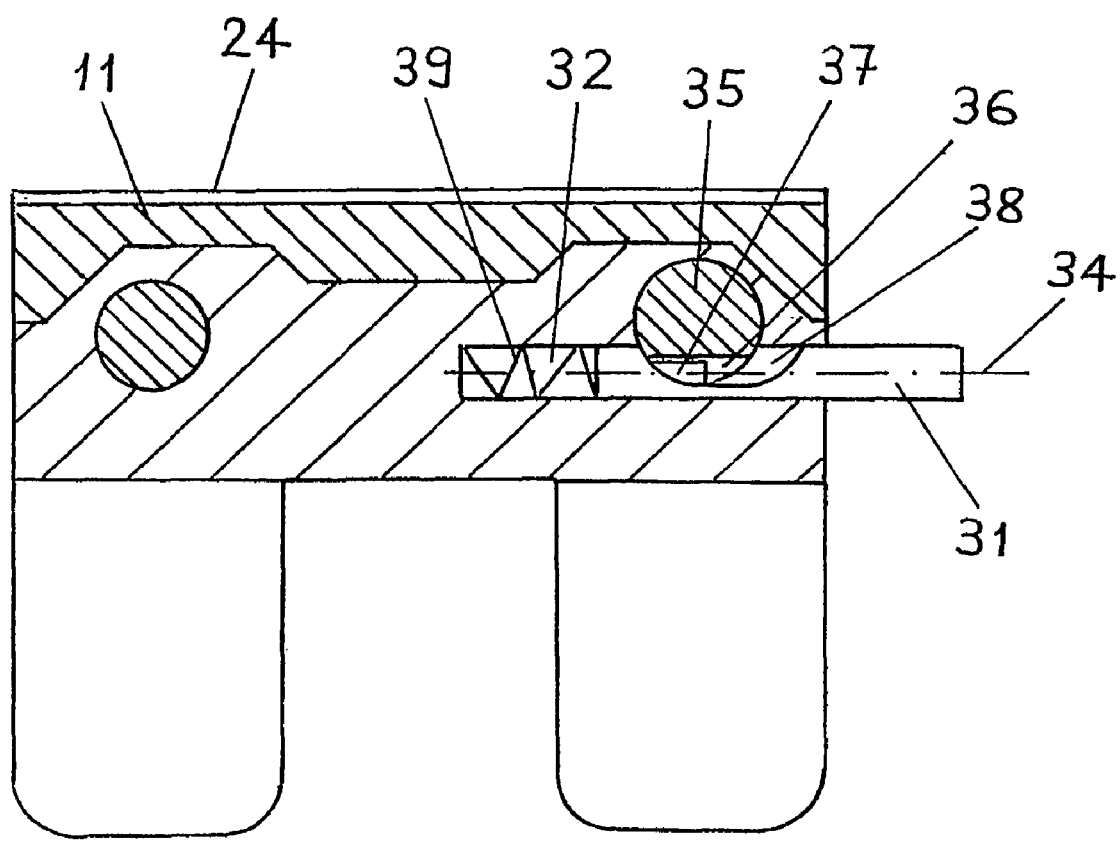
FIG. 4 is a sectional view of the embodiment of the device according to the invention shown in FIGS. 1 and 2.

FIG. 4 shows an example of one of the location pins 31 which is lodged in the first transverse bore 32 of the second plate 10 in such a way as to be displaceable coaxially to the bore axis 34. In the bottom end portion of the first transverse bore 32, a spring 39 is inserted which presses the location pin 31 against the pin 35. The location pin 31 is provided with a recess 38 including a cam 37 protruding from this recess 38. The cam 37 extends only over part of the axial length of the recess 38. In a first position, the location pin 31 is urged against the pin 35 by the elastic force of the spring 39, so that the recess 38 which partially surrounds the pin 35 on its periphery is axially displaced to such an extent relative to the pin 35 that the cam 37 engages with one of the grooves 36. In a second position, into which the location pin 31 may for example be axially pushed by hand against the elastic force of the spring 39, the recess 38 which partially surrounds the pin 35 is displaced to such an extent relative to the pin 35 that the cam 37 is axially released from the groove 36 with respect to the bore axis 34 and that the pin 35 is displaceable parallel to the central axis 19. The embodiment of the location pin 31 including a recess 38, a cam 37, and a spring 39, as set forth in connection with the present example is also valid for the other location pins 31 used with the device according to the invention (FIG. 1).

The invention claimed is:

1. A device for determining optimal dimensions of components of a knee endoprosthesis, including
   A) an angular element (7) comprising a first plate (9) and a second plate (10), said first plate defining a plate longitudinal axis (8), said second plate being arranged at a right angle to said first plate and defining a central axis (19) extending perpendicularly to the first plate (9); and
   B) a first caliper (16) that is releasably fastened on the second plate (10) in a manner that permits said first caliper to be displaced parallel to the central axis (19), said first caliper having a bearing surface (25) extending essentially parallel to the first plate (9) for resting against a tibial plateau (29) when a knee joint is bent,
   C) said first plate (9) comprising a bottom surface (17), a top surface (18), a first end portion (12) intersecting the plate longitudinal axis (8), and a second end portion (13) intersecting the plate longitudinal axis (8);
   D) said second plate (10) comprising a top end portion (14), a bottom end portion (15), and a substantially planar inner side (23) adjoining the second end portion (13) so that the angular element (7) may be connected to the femur (5) in such a way that the inner side (23) may be brought to rest against a distal end face (28) of the femur and the first plate (9) is arranged anteriorly to the femur (5) with the plate longitudinal axis (8) extending parallel to a longitudinal axis of the femur (5);
   E) a second caliper (11) having a second bearing surface (24) extending substantially parallel to the inner side (23) and designed to rest against the tibial plateau (29) when the knee joint is straightened, said second bearing surface, with the second end portion (13), is displaceable parallel to the longitudinal axis (8) and releasably fastenable on the first plate (9);
   F) a first inlay (22) having a bottom end face (27) facing the first caliper (16), said first inlay (22) being arranged between the bottom end portion (15) and the first caliper (16) so as to be displaceable coaxially with the central axis (19) and releasably fastenable on the second plate (10), said first caliper (16) being displaceable relative to the first inlay (22); and
   G) a second inlay (21) having an anterior end face (26) facing the second caliper (11), said second inlay (21) being arranged between the second end portion (13) and the second caliper (11) so as to be displaceable coaxially to the plate longitudinal axis (8) and releasably fastenable on the first plate (9), said second caliper (11) being displaceable relative to the second inlay (21).

2. The device according to claim 1, wherein the second caliper (11) comprises positioning means (20) that are arranged on a straight line extending parallel to the plate longitudinal axis (8) and are spaced apart from one another in axial succession by a distance $a_i$, whereby the second bearing surface (24) is fastenable at defined distances ($A_i = \Sigma a_j$; j=1 to N) relative to the anterior end face (26).

3. The device according to claim 1, wherein the first caliper (16) comprises positioning means (20) that are arranged on a straight line extending parallel to the central axis (19) and are spaced apart from one another in axial succession by a distance $a_j$, whereby the first bearing surface (25) is fastenable at a defined distance ($A_i = \Sigma a_j$; j=1 to N) relative to the bottom end face (27).

4. The device according to claim 1, wherein the second inlay (21) comprises positioning means (20) that are arranged on a straight line extending parallel to the plate longitudinal axis (8) and are spaced apart from one another in axial succession by a distance $b_j$, whereby the anterior end face (26) is fastenable at defined distances ($B_i = \Sigma b_j$; j=1 to M) relative to the second end portion (13).

5. The device according to claim 1, wherein the first inlay (22) comprises positioning means (20) that are arranged on a straight line extending parallel to the central axis (19) and are spaced apart from one another in axial succession by a distance $c_j$, whereby the bottom end face (27) is fastenable at defined distances ($C_i = \Sigma c_j$; j=1 to Q) relative to the bottom end portion (15).

6. The device according to claim 2, wherein the defined distances $A_i$ correspond to the different, standardized thicknesses of an inlay (2) of the tibial component of a knee endoprosthesis.

7. The device according to claim 4, wherein the defined distances $B_i$ correspond to the different, standardized thicknesses of a spacer (3) for the femoral component (1) of a knee endoprosthesis.

8. The device according to claim 5, wherein the defined distances $C_i$ are adjustable corresponding to the different, standardized A/P sizes (30) of a femoral component (1) of a knee endoprosthesis.

9. The device according to claim 1, wherein:
A) the first inlay (22) comprises a top end portion (41) and, extending between the bottom end face (27) and the top end portion (41) and arranged axially adjacent to one another, a sleeve (40) and a pin (35), the sleeve (40) adjoining the bottom end face (27) and a sleeve bore (43) being open towards the bottom end face (27);
B) the second inlay (21) comprises a posterior end portion (42) and, extending between the anterior end face (26) and the posterior end portion (42) and arranged axially adjacent to one another, a sleeve (40) and a pin (35), the sleeve (40) adjoining the anterior end face (26) and a sleeve bore (43) being open towards the anterior end face (26);
C) the first plate (9) comprises a first guide bore (44) extending coaxially to the plate longitudinal axis (8) and designed to receive the second inlay (21) so as to be axially displaceable;
D) the second plate (10) comprises a second guide bore (45) extending parallel to the central axis (19) and designed to receive the first inlay (22) so as to be axially displaceable; and
E) the first and second calipers (16;11) each comprise a guide bolt (46) facing the first and second bearing surfaces (25;24), respectively,
F) the guide bolts (46) are receivable, by way of axial displacement, within the sleeve bores (43).

10. The device as claimed in claim 9, wherein:
A) the pins (35) and the guide bolts (46) are provided with grooves (36) that serve as the positioning means (20) and extend crosswise to the plate longitudinal axis (8) and the central axis (19), respectively;
B) wherein axial arresting of the first and second inlays (22;21) relative to the first and second plates (9;10), respectively, is provided by location pins (31) that are received, in an axially displaceable manner within the first and second plates (9;10), by first transverse bores (32) having bore axes (34) extending crosswise to the plate longitudinal axis (8) and to the central axis (19), respectively, said location pins being capable of engaging with the grooves (36) formed in the pins (35);
C) wherein axial arresting of the first and second calipers (16;11) relative to the first and second inlays (22;21) is provided by location pins (31) that are received in an axially displaceable manner within second transverse bores (51) formed in the first and second inlays (22;21) and may be brought to engage with the grooves (36) formed in the guide bolts (46);
D) the first and second plates (9;10) are provided with elongated holes (33) having their longitudinal dimensions parallel to the plate longitudinal axis (8) and to the central axis (19), respectively, said elongated holes receive the location pins (31), 50 that the first and second inlays (22;21) with arrested first and second calipers (16;11) are nonetheless displaceable relative to the first and second plates (9;10); and
E) the location pins (31) comprise radial recesses (38) including cams (37) protruding from the recesses (38), the cams (37) extending only over part of the axial length of the recesses (38), 50 that the location pins (31) may be moved into a first position, in which the cams (37) are in engagement with the grooves (36), and into a second position, in which the cams (37), by axial displacement of the location pins (31), are axially released from the grooves (36), and the pins (35) and guide bolts (46) are displaceable coaxially to the plate longitudinal axis (8) and parallel to the central axis (19), respectively.

* * * * *

UNITED STATES PATENT AND TRADEMARK OFFICE
CERTIFICATE OF CORRECTION

PATENT NO. : 7,101,377 B2  Page 1 of 1
APPLICATION NO. : 10/362147
DATED : September 5, 2006
INVENTOR(S) : Cortellessa et al.

It is certified that error appears in the above-identified patent and that said Letters Patent is hereby corrected as shown below:

Column 8, Line 39 (Claim 10, Line 26), delete "50" and insert --so--.

Column 8, Line 46 (Claim 10, Line 33), delete "50" and insert --so--.

Signed and Sealed this

Second Day of January, 2007

JON W. DUDAS
*Director of the United States Patent and Trademark Office*